United States Patent [19]
Taylor

[11] 4,106,675
[45] Aug. 15, 1978

[54] LIQUID SAMPLING DEVICE

[75] Inventor: Glenn N. Taylor, Cary, Ill.

[73] Assignee: The Kendall Company, Boston, Mass.

[21] Appl. No.: 753,113

[22] Filed: Dec. 22, 1976

[51] Int. Cl.² .................. B65D 47/26; F16K 31/14
[52] U.S. Cl. ............................... 222/556; 128/227; 251/342
[58] Field of Search ............... 251/342, 4; 73/422 R; 222/556; 128/275, 2 F, 295, 227, 274, 226

[56] References Cited

U.S. PATENT DOCUMENTS

| | | | |
|---|---|---|---|
| 2,518,165 | 8/1950 | Millard | 128/226 X |
| 3,415,299 | 12/1968 | Hinman, Jr. et al. | 150/1 X |
| 3,473,532 | 10/1969 | Eisenberg | 128/227 |
| 3,916,948 | 11/1975 | Benjamin | 251/342 X |

Primary Examiner—Joseph F. Peters, Jr.
Assistant Examiner—Norman L. Stack
Attorney, Agent, or Firm—Powell L. Sprunger

[57] ABSTRACT

A liquid sampling device having, a tubular section of flexible material having a wall defining a lumen for passage of liquid. The device has a flow control element including a rigid valve member positioned in the lumen of the tubular section, with the valve member having an outer sealing surface sealingly engaging against an inner surface of the tubular section. The tubular section deforms when squeezed from opposed directions against the valve member to permit passage of a liquid sample between the valve member and an inner surface of the tubular section.

14 Claims, 17 Drawing Figures

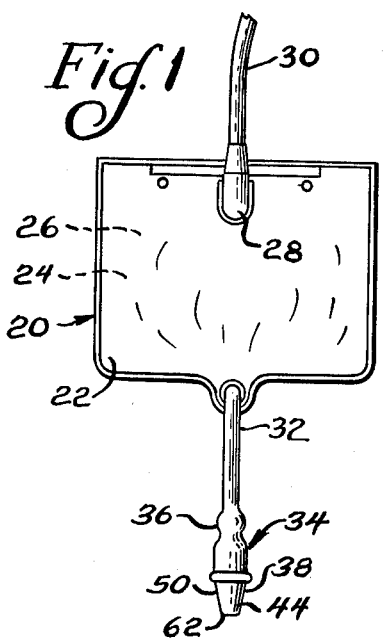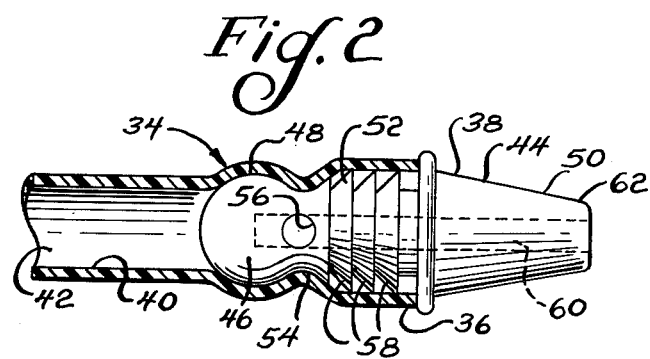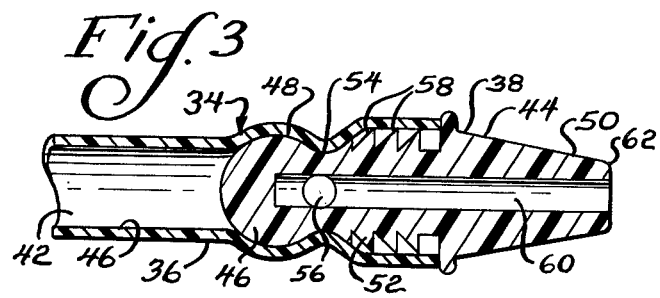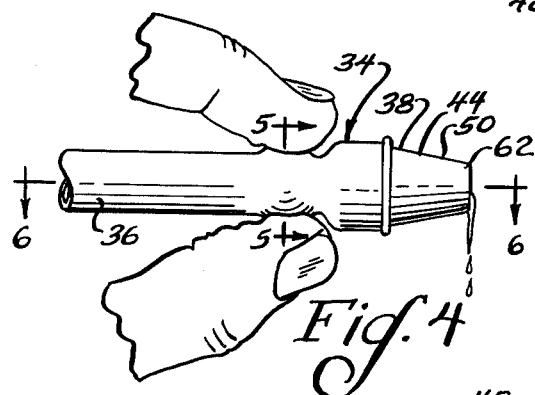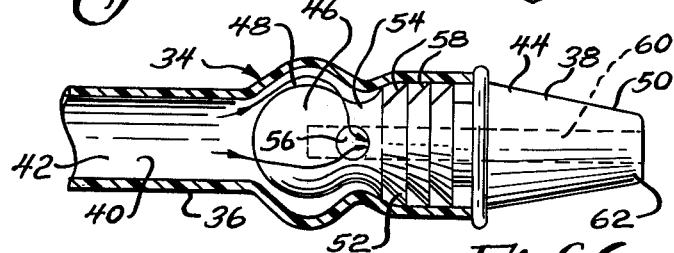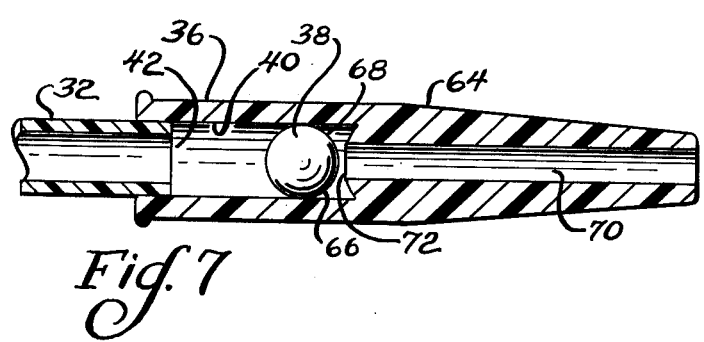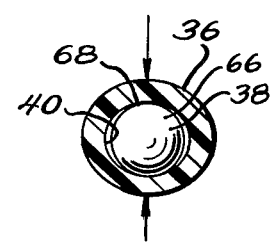

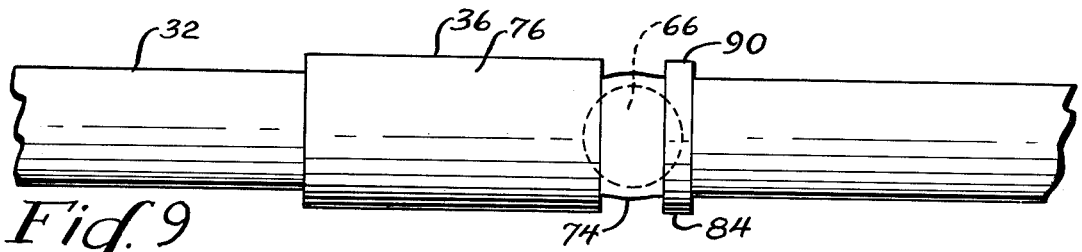
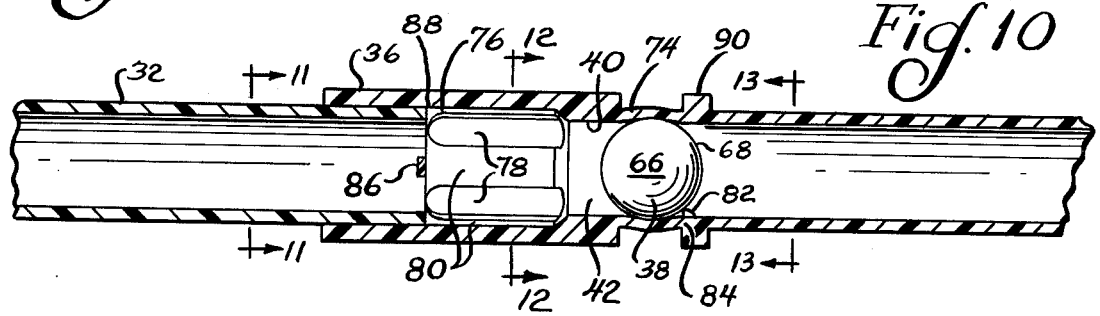
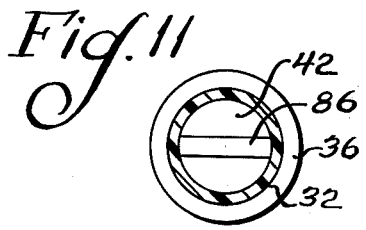
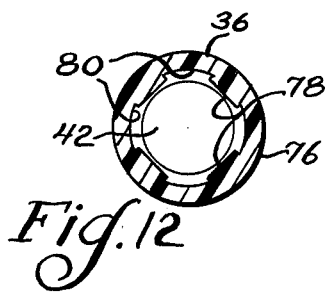
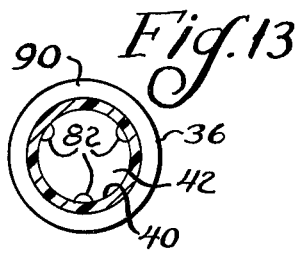
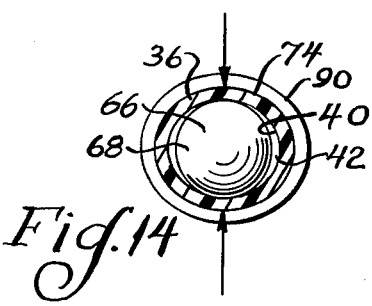
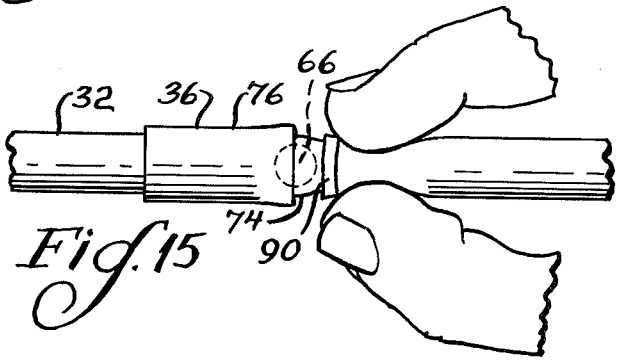
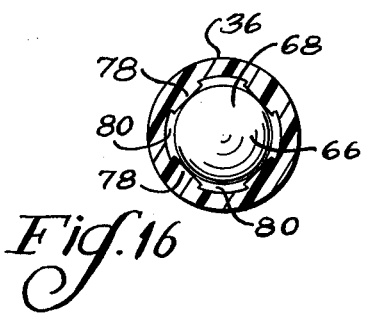
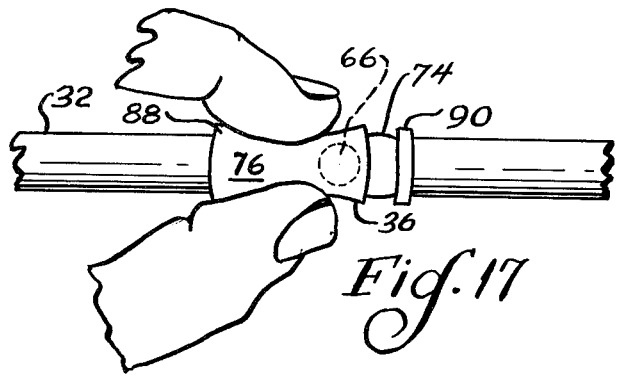

LIQUID SAMPLING DEVICE

BACKGROUND OF THE INVENTION

The present invention relates to liquid flow control device, and more particularly to such devices for obtaining a liquid sample.

In the past, drainage bags have been used to collect urine from a patient during catheterization. According to standard procedures, a catheter is positioned in the urethra of the patient, and urine drains through the catheter and a drainage tube, which is connected to the catheter, into a chamber in the bag for collection therein. Although such bags may satisfactorily collect the urine, it may be necessary to periodically obtain a small urine sample for purposes of analysis, and the prior art bags have rendered such a sampling procedure relatively difficult. For example, such bags have been commonly provided with a drain tube having a clamp or valve which is designed primarily to drain all of the collected urine from the bag through the drain tube. When it is desired to obtain a sample, a suitable receptacle is positioned beneath the drain tube and the clamp or valve is opened. However, prior clamps and valves used for this purpose are difficult to manipulate with one hand, and when opened, permit passage of an amount of liquid which is excessive for sampling purposes. Thus, it is desirable that a relatively samll quantity of urine sample may be obtained during catheterization.

SUMMARY OF THE INVENTION

A principal feature of the present invention is the provision of a device of simplified construction for obtaining a liquid sample.

The sampling device of the present invention comprises a tubular section of flexible material having a wall defining a lumen for passage of liquid. The device has a flow control element comprising, a rigid valve member positioned in the lumen of the tubular section, with the valve member having an outer sealing surface sealingly engaging against an inner surface of the sampling section.

A feature of the present invention is that the valve member normally prevents passage of liquid through the lumen.

Another feature of the invention is that the tubular section may be squeezed against the valve member in order to deform the flexible wall of the tubular section.

Thus, a feature of the invention is that the deformed wall permits passage of a liquid sample between the valve member and the tubular section.

A feature of the invention is that the liquid sample may be obtained in a simplified manner by merely squeezing the tubular section through use of one hand.

Yet another feature of the invention is that in an embodiment the valve member comprises a generally spherical ball, and the ball may be moved in the tubular section to a spaced position where the tubular section has larger internal dimensions than the ball.

Thus, another feature of the invention is that the device permits drainage of liquid between the ball and tubular section when the ball is located at the spaced position.

Still another feature of the invention is that the ball may be moved between its sealing and drainage configurations by merely squeezing the tubular section against the ball.

Further features will become more fully apparent in the following description of the embodiments of this invention and from the appended claims.

DESCRIPTION OF THE DRAWINGS

In the drawings:

FIG. 1 is a fragmentary plan view of a drainage bag having a liquid sampling device of the present invention;

FIG. 2 is a fragmentary view, taken partly in section, of the liquid sampling device of FIG. 1;

FIG. 3 is a fragmentary sectional view of the sampling device of FIG. 2;

FIG. 4 is a fragmentary plan view illustrating use of the device to obtain a sample;

FIG. 5 is a sectional view taken substantially as indicated along the line 5—5 of FIG. 4;

FIG. 6 is a fragmentary view taken partly in section and being taken substantially as indicated along the line 6—6 of FIG. 4;

FIG. 7 is a fragmentary view, taken partly in section, of another embodiment of the liquid sampling device of the present invention;

FIG. 8 is a view, taken partly in section, showing deformation of a wall in the device of FIG. 7 during use;

FIG. 9 is a fragmentary elevational view of another embodiment of the flow control device of the present invention;

FIG. 10 is a fragmentary view, taken partly in section, of the device of FIG. 9;

FIG. 11 is a sectional view taken substantially as indicated along the line 11—11 of FIG. 10;

FIG. 12 is a sectional view taken substantially as indicated along the line 12—12 of FIG. 10;

FIG. 13 is a sectional view taken substantially as indicated along the line 13—13 of FIG. 10;

FIG. 14 is a view, taken partly in section, showing use of the device of FIG. 9 to obtain a liquid sample;

FIG. 15 is a fragmentary elevational view illustrating use of the device while moving a flow control element from a sealing to drainage position;

FIG. 16 is a view, taken partly in section, showing the flow control element in the drainage position; and FIG. 17 is a fragmentary elevational view illustrating use of the device while moving the flow control element from the drainage to sealing position.

DESCRIPTION OF THE PREFERRED EMBODIMENTS

Referring now to FIG. 1, there is shown a drainage bag generally designated 20 having a pair of opposed side walls 22 and 24 defining a liquid collection chamber 26 in the bag 20. The bag 20 has a drip chamber 28 connected to the side wall 22 and communicating with the collection chamber 26. The drainage bag also has a drainage tube 30 connected to the drip chamber 28 and communicating with the collection chamber 26 through the drip chamber 28. During catheterization, a urinary catheter (not shown) is positioned in the urethra of a patient with a distal end of the catheter located in the patient's bladder and with a proximal end of the catheter located outside the patient's body. The proximal end of the catheter is connected to an upstream portion of the drainage tube 30, and urine drains from the bladder through the catheter, drainage tube and the drip chamber 28 into the bag chamber 26 for collection therein. The bag 20 also has a conduit 32 connected to the side wall 22 and communicating with a lower portion of the bag chamber 26. As will be seen below, the conduit 32 is provided with a sampling device generally designated 34 which permits a liquid sample to be obtained from the collection chamber 26.

With reference to FIGS. 1–3, the conduit 32 has a tubular section 36 at an outer end of the conduit. The tubular section is made from a flexible material, such as polyvinylchloride or rubber, and has an inner surface 40 defining a lumen 42. The sampling device 34 has a flow control element 38 comprising a rigid valve member 44 secured to an outer end of the conduit or tubular section 36. The valve member 44 may be made of any suitable material, such as polyethylene.

The valve member 44 has a partially spherical inner portion 46 positioned in the lumen 42 of the tubular section 36, with the inner portion 46 having a larger diameter than the inner diameter of the tubular section 36, such that the inner portion 46 has a peripheral surface 48 sealingly engaging against the inner surface 40 of the tubular section 36. The valve member 44 also has an outer portion 50 extending from the tubular section 36, and a central portion 52 extending between the inner portion 46 and the outer portion 50. As shown, the central portion 52 has a region 54 of reduced dimensions relative the inner portion 46, and at least one opening 56 in the region 54 facing the inner surface 42 of the tubular section 36. The central portion 52 has a plurality of annular pointed flanges 58 which have a greater diameter than the internal diameter of the tubular section 36, in order that the flanges 58 sealingly engage against the inner surface 40 of the tubular section 36 and retain the valve member 44 in place in the tubular section. As shown, the central portion 52 and outer portion 50 have a longitudinally extending channel 60 which communicates with the opening or openings 56 and which extends through the central portion 52 and outer portion 50 to an outer end 62 of the valve member 44.

In the normal configuration of the sampling device 34, as shown in FIGS. 2 and 3, the peripheral surface 48 of the valve member 44 sealingly engages against the inner surface 40 of the tubular section 36, and prevent passage of liquid from the lumen 42 into the opening or openings 56 of the valve member 44. When it is desired to obtain a liquid sample, with reference to FIGS. 4–6, the wall portion of the tubular section 36 which overlies the inner portion 46 of the valve member 44 may be squeezed on opposed sides against the inner portion 46, such that the flexible wall of the tubular section deforms at locations between the points where the tubular section is squeezed. Thus, as shown in FIGS. 5 and 6, portions of the tubular section 36 between the squeezed locations become spaced from the inner portion 46 of the valve member 44, and a liquid sample is permitted to pass between the inner portion 46 of the valve member 44 and the inner surface 40 of the tubular section 36, as indicated by the direction of the arrows in FIG. 6. The liquid sample then passes through the opening or openings 56 of the valve member 44 in the region 54, and through the channel 60 of the valve member where it may be collected in a suitable receptacle as it passes from the outer end of the valve member 44. In this manner, a liquid sample may be readily obtained by merely squeezing the tubular section against the valve member with the fingers of one hand, while the receptacle may be held with the other hand to receive the specimen. After a sufficient sample has been collected, the tubular section may be released, and the tubular section 36 again assumes its sealing configuration against the valve member 44 to prevent passage of liquid through the liquid sampling device 34.

Another embodiment of the present invention is illustrated in FIGS. 7 and 8, in which like reference numerals designate like parts. In this embodiment, the tubular section 36 comprises a nozzle 64 of flexible material, such as polyvinylchloride, which is attached to an outer end of the conduit 32. The tubular section 36 has an inner surface 40 defining a lumen, as previously described. In this embodiment, the flow control element 38 comprises a spherical ball which is made of a rigid material, such as polyethylene. As shown, the ball 66 is positioned in the lumen 42, and has a larger diameter than the internal diameter of the tubular section 36, such that an outer surface 68 of the ball 66 sealingly engages against the inner surface 40 of the tubular section 36 to prevent passage of liquid through the lumen. The tubular section 36 also has a channel 70 of smaller dimensions than the lumen 42 and communicating with the lumen 42 through an opening 72 facing the ball 66, with the ball 66 being slightly spaced from the opening 72.

In use, the tubular section 36 may be squeezed against the ball 66 in a manner as previously described in connection with the sampling device of FIGS. 1–6, and the flexible wall of the tubular section deforms, as shown in FIG. 8, such that opposed spacings are defined between the outer surface 68 of the ball 66 and the inner surface 40 of the tubular section 36. Thus, a liquid sample is permitted to pass between the ball 66 and the inner surface 40 of the tubular section 36, after which the sample passes through the opening 72 and the channel 70 of the tubular section to the outer end of the tubular section where it may be collected in a suitable receptacle. After a sufficient quantity of sample has been collected, the tubular section is released, and the flexible wall again assumes its sealing configuration against the ball 66 to prevent passage of liquid through the lumen 42.

Another embodiment of the present invention is illustrated in FIGS. 9–17, in which like reference numerals designate like parts. In this embodiment, the tubular section 36 is attached to an end of the conduit 32 and has an inner surface 40 defining a drainage lumen 42, as previously described. With reference to FIGS. 9–13, the flow control element 38 comprises a rigid spherical ball 66 which is positioned in the lumen 42. The tubular section 36 has a first portion or longitudinal section 74 which has an internal diameter slightly less than the diameter of the ball 66. The tubular section 36 also has a second portion or longitudinal section 76 which is located upstream relative the first portion 74. The second portion 76 has a plurality of spaced longitudinally extending ribs 78 which have inner dimensions approximately equal to the diameter of the ball 66. The spaced ribs 78 define a plurality of longitudinally extending grooves 80 which are recessed from the inner surfaces of the ribs 78 and which have larger dimensions than the diameter of the ball 66. The tubular section 36 also has a plurality of inwardly directed bosses 82 projecting into the lumen 42 and located adjacent an end 84 of the first portion 74 remote the second portion 76 to prevent passage of the ball 66 downstream from the first portion 74 of the tubular section 36. In addition, the tubular section 36 has a bar 86 extending across the lumen 42 and located adjacent an end 88 of the second portion 76 remote the first portion 74 to prevent passage of the ball 66 upstream from the second portion 76 into the conduit 32. The tubular section 36 also has an annular flange 90 extending outwardly from the tubular section adjacent the end 84 of the first portion 74 for a purpose which will be described below.

In use, with reference to FIG. 10, the ball 66 is located in the first portion 74 of the tubular section 36 at a first control or sealing position of the ball 66 where the outer surface 68 of the ball 66 sealingly engages against the inner surface 40 of the first portion 74 and thus prevents passage of liquid through the lumen 42. When it is desired to obtain a liquid sample, the first portion 74 of the tubular section 36 is squeezed on opposed sides, as shown in FIG. 14, in order to deform the wall of the first portion 74. Thus, the wall of the first portion 74 becomes spaced from the outer surface 68 of the ball 66 and permits passage of a liquid sample between the ball 66 and the inner surface 40 of the first portion 74. In this manner, a liquid sample may be readily obtained by merely pressing opposed sides of the first portion 74 of the tubular section 36. When a sufficient quantity of the liquid sample has been obtained, the first portion 74 of the tubular section 36 may be released, and the wall again assumes its sealing configuration against the outer surface 68 of the ball 66 to prevent passage of liquid through the lumen.

When it is desired to drain liquid through the tubular section, with reference to FIG. 15, the tubular section 36 may be pressed by the user's fingers adjacent or on the flange 90 in order to squeeze the ball at the end 84 of the first portion 74 and move the ball 66 from its first control position in the first portion 74 toward a second control position in the second portion 76 of the tubular section 36. Thus, the tubular section 36 is continuously squeezed on one side of the ball remote the second portion 76 until the ball 66 assumes its second control position in the second portion 76, at which time the ball 66 is located beneath the longitudinally extending ribs 78, as shown in FIG. 16. In this configuration, liquid passes through the channels or grooves 80 and around the ball in the lumen 42 to permit drainage of the liquid through the tubular section 36.

When the liquid has drained through the lumen 42, the ball 66 may be moved from the second control position to the first control position as follows. With reference to FIG. 17, the tubular section may be pressed by the user's fingers adjacent the end 88 of the second portion 76 remote the first portion 74 in order to move the ball along the tubular section into its first control position in the first portion 74. In this configuration, the outer surface 68 of the ball 66 again sealingly engages against the inner surface 40 of the first portion 74 in order to prevent passage of liquid through the lumen 42 of the tubular section 36, as shown in FIG. 10. Thus, according to the present invention, a sample of liquid may be readily obtained by squeezing the first portion 74 of the tubular section 36 when the ball 66 is located at its first control position, and the ball may be moved to its second position in the second portion 76 of the tubular section in order to permit drainage of liquid through the tubular section 36.

The foregoing detailed description is given for clearness of understanding only, and no unnecessary limitations should be understood therefrom, as modifications will be obvious to those skilled in the art.

I claim:

1. A drainage bag, comprising:
   a receptacle having a liquid collection chamber;
   a conduit connected to said receptacle and communicating with a lower portion of said chamber for draining liquid from the receptacle chamber, said conduit including a sampling section of flexible material having a wall defining a lumen and an outer surface adapted to be squeezed by a user's fingers; and
   a flow control element comprising, a rigid valve member positioned in the lumen of said sampling section, said valve member having an outer sealing surface sealingly engaging against an inner surface of the sampling section, said sampling section deforming when said wall surface is squeezed from opposed directions against the valve member to permit passage of a liquid sample between the valve member and an inner surface of the sampling section, said valve member being secured in the lumen at an outer end of the sampling section and said valve member having an extension defining a nozzle for the conduit and a passageway communicating between an end of the nozzle and an outer surface of the valve member intermediate its ends.

2. The bag of claim 1 wherein the sealing surface of said valve member is defined by a generally spherical portion of the valve member.

3. The bag of claim 1 wherein the sealing surface of said valve member is generally circular.

4. A liquid sampling device, comprising:
   a tubular section of flexible material having a wall defining a lumen for passage of liquid and an outer surface adapted to be squeezed by a user's fingers; and
   a flow control element comprising, a rigid valve member secured to an end of said tubular section, said valve member having a partially spherical inner portion positioned in said lumen and having a greater diameter than the inner diameter of the tubular section, said inner portion having a peripheral surface sealingly engaging against an inner surface of the tubular section, said valve member having an outer portion extending from the tubular section, and a central portion extending between said inner and outer portions, said central portion having a region of reduced dimensions relative said inner portion, an opening at an outer surface of the central portion facing the inner surface of the tubular section, and means sealingly engaging against the inner surface of the tubular section at a location intermediate said opening and said outer portion of the valve member, said central and outer portions of the valve member having a channel communicating with said opening and extending through said outer valve member portion, said wall surface of the tubular section being squeezed against the valve member inner portion to deform said wall and permit passage of a liquid sample between said inner portion and tubular section and through said opening and channel to the outside of the valve member.

5. The device of claim 4 wherein said engaging means comprises at least one circumferential flange sealingly engaging against the inner surface of said tubular section.

6. The device of claim 4 wherein said opening is located in said region.

7. A liquid sampling device, comprising:
   a generally spherical rigid ball; and a tubular section of flexible material having a wall defining a lumen for passage of liquid, said tubular section having a first portion having an internal diameter slightly less than the diameter of the ball, and a separate second portion having internal dimensions greater than the diameter of the ball in a least a part of the second portion, said ball being received in said lumen to control the passage of liquid through the tubular section, said ball being located in said first portion at a first control position to sealingly engage against the inner surface of said first portion and prevent passage of liquid through the lumen, said first portion being squeezed against said ball to deform a wall of said first portion and permit passage of a liquid sample between the ball and an inner surface of said first portion, said ball being located in said second portion at a second control position to permit drainage of liquid between the ball and said tubular section, said tubular section being squeezed on a side of said first portion remote said second portion with the ball at said first control position to move the ball toward said second control position, and said tubular section being squeezed on a side of said second portion remote the first portion with the ball at said second control position to move the ball toward said first control position, said second portion comprising a longitudinal section of the tubular section having a plurality of longitudinally extending ribs defining an inner surface with dimensions approximately equal to the diameter of said ball, said ribs defining a plurality of longitudinally extending grooves recessed from the inner surface of said ribs to permit passage of liquid therethrough with said ball located in said second control position.

8. The device of claim 7 wherein said first portion of the tubular section is located downstream relative said second portion.

9. The device of claim 7 including means for preventing movement of said ball past said first control position in said first portion.

10. The device of claim 9 wherein said preventing means comprises at least one inner boss of the tubular section projecting into said drainage lumen adjacent an end of said first portion remote said second portion.

11. The device of claim 7 wherein said first portion comprises a generally cylindrical section of said tubular section.

12. The device of claim 7 including means for preventing movement of said ball past said second control position in said second portion.

13. The device of claim 12 wherein the preventing means comprises a bar extending across said lumen adjacent an end of said second portion remote said first portion.

14. The device of claim 7 including an annular flange extending outwardly from the tubular section adjacent an end of said first portion remote the second portion to facilitate movement of said ball from said first to second control position.

* * * * *